United States Patent [19]
Jaetsch et al.

[11] Patent Number: 5,744,478
[45] Date of Patent: Apr. 28, 1998

[54] THIAZOLO [3,2-A] QUINOLINE AND THIAZOLO [3,2-A] NAPHTHYRIDINE DERIVATIVES

[75] Inventors: Thomas Jaetsch, Köln; Werner Hallenbach, Monheim; Thomas Himmler, Odenthal; Klaus-Dieter Bremm, Recklinghausen; Rainer Endermann, Wuppertal; Franz Pirro, Langenfeld, all of Germany; Michael Stegemann, Kansas City, Mo.; Heinz-Georg Wetzstein, Leverkusen, Germany

[73] Assignee: Bayer Aktiengesellschaft, Leverkusen, Germany

[21] Appl. No.: 793,795

[22] PCT Filed: Aug. 21, 1995

[86] PCT No.: PCT/EP95/03315

§ 371 Date: Feb. 21, 1997

§ 102(e) Date: Feb. 21, 1997

[87] PCT Pub. No.: WO96/06848

PCT Pub. Date: Mar. 7, 1996

[30] Foreign Application Priority Data

Sep. 1, 1994 [DE] Germany .................. 44 31 122.2

[51] Int. Cl.⁶ .................. A61K 31/435; A61K 31/535; C07D 513/04; C07D 519/00
[52] U.S. Cl. .................. 514/291; 514/222.8; 514/229.5; 546/80; 546/83; 546/84; 544/14; 544/99
[58] Field of Search .................. 546/80, 84, 83; 514/291, 292, 222.8, 229.5; 544/14, 99

[56] References Cited

FOREIGN PATENT DOCUMENTS

| 0193283 | 9/1986 | European Pat. Off. . |
| 0286089 | 10/1988 | European Pat. Off. . |
| 0596126 | 5/1994 | European Pat. Off. . |

OTHER PUBLICATIONS

Chemical Abstracts, vol. 117, No. 11, Abstract No. 111, 597d.

*Primary Examiner*—Zinna Northington Davis
*Attorney, Agent, or Firm*—Sprung Kramer Schaefer & Briscoe

[57] ABSTRACT

The present invention relates to new thiazolo[3,2-a] quinoline and thiazolo[3,2-a]naphthyridine derivatives of the general formula (I)

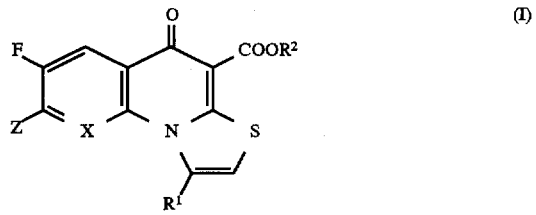

in which $R^1$, $R^2$, Z and X have the meaning indicated in the description, processes for their preparation and their use in antibacterial compositions.

7 Claims, No Drawings

THIAZOLO [3,2-A] QUINOLINE AND THIAZOLO [3,2-A] NAPHTHYRIDINE DERIVATIVES

This application is a 371 of PCT/EP95/03315 filed Aug. 21, 1995.

The present invention relates to new thiazolo[3.2-a] quinoline derivatives, processes for their preparation, and antibacterial compositions containing these derivatives.

It has already been disclosed that thiazoloquinolinecarboxylic acids have antibacterial activity. Examples for this are found in EP-O 286 089, EP-0 387 877, EP-0 472 826 and in the Journal of Medicinal Chemistry 36, 2621 (1993).

There have now been found compounds of the general formula (I)

in which $R^1$ represents hydrogen or methyl which is optionally substituted by halogen or methoxy, $R^2$ represents hydrogen, alkyl having 1 to 4 carbon atoms which is optionally substituted by hydroxyl, methoxy, amino, methylamino or dimethylamino, or (5-methyl-2-oxo-1,3-dioxol-4-yl)methyl, X represents nitrogen or C—$R^4$, wherein $R^4$ represents hydrogen, halogen or methoxy or together with $R^1$ can form a bridge of the structure —O—$CH_2$— or —S—$CH_2$—, Z represents the radicals of the structures wherein $R^5$ represents hydrogen, hydroxyl, —$NR^{10}R^{11}$, hydroxymethyl, —$CH_2$—$NR^{10}R^{11}$, carboxyl, methoxycarbonyl or ethoxycarbonyl, where $R^{10}$ represents hydrogen, $C_1$–$C_3$-alkyl, which is optionally substituted by hydroxyl, alkoxycarbonyl having 1 to 4 C atoms in the alkoxy moiety or $C_1$–$C_3$-acyl, $R^{11}$ represents hydrogen or methyl, $R^6$ represents hydrogen, straight-chain or branched $C_1$–$C_3$-alkyl or cyclopropyl, $R^7$ represents hydrogen or methyl, $R^8$ represents hydrogen or methyl, $R^9$ represents hydrogen, methyl or radicals of the structures —CH=CH—$COOR^{9'}$, —$CH_2$—$CH_2$—$COOR^{9'}$, —$CH_2$—CO—$CH_3$, —$CH_2$—$CH_2$—CN $R^{9'}$ represents methyl or ethyl, B represents —$CH_2$—, O or a direct bond.

The compounds of the formula (I) can be present in the form of racemates or as enantiomerically pure compounds and also in the form of their pharmaceutically utilizable hydrates and acid addition salts and also in the form of their alkali metal, alkaline earth metal, silver and guanidinium salts.

The compounds of the formula (I) are obtained when compounds of the formula (II)

in which $R^1$, $R^2$ and X have the meaning indicated above and

Y represents fluorine or chlorine, are reacted with compounds of the formula (III)

Z-H     (III), in which

Z has the meaning indicated above, if appropriate in the presence of acid scavengers.

In comparison with known representatives of this structural type, the compounds according to the invention have a higher antibacterial action, in particular in the gram-positive region. They are therefore suitable as active compounds for human and veterinary medicine, where for veterinary medicine the treatment of fish for therapy or prevention of bacterial infections is also to be included.

Preferred compounds of the formula (I) are those in which $R^1$ represents hydrogen or methyl, $R^2$ represents hydrogen, alkyl having 1 to 4 carbon atoms, which is optionally substituted by hydroxyl, methoxy, amino, methylamino or dimethylamino, or (5-methyl-2-oxo-1,3-dioxol-4-yl)methyl, X represents nitrogen or C—$R^4$, wherein $R^4$ represents hydrogen, halogen or methoxy or together with $R^1$ can form a bridge of the structure —O—$CH_2$— or —S—$CH_2$—, Z represents radicals of the structures wherein $R^5$ represents hydrogen, hydroxyl, —$NR^{10}R^{11}$, hydroxymethyl, —$CH_2$—$NR^{10}R^{11}$, where $R^{10}$ represents hydrogen, $C_1$–$C_2$-alkyl which is optionally substituted by hydroxyl, alkoxycarbonyl having 1 to 4 C atoms in the alkoxy moiety or $C_1$–$C_3$-acyl, $R^{11}$ represents hydrogen or methyl, $R^6$ represents hydrogen, straight-chain or branched $C_1$–$C_3$-alkyl or cyclopropyl, $R^7$ represents hydrogen or methyl, $R^8$ represents hydrogen, $R^9$ represents hydrogen or methyl, B represents —$CH_2$—, O or a direct bond, and their pharmaceutically utilizable hydrates and acid addition salts and also the alkali metal, alkaline earth metal, silver and guanidinium salts of the carboxylic acids on which they are based.

Particularly preferred compounds of the formula (I) are those i which $R^1$ represents methyl, $R^2$ represents hydrogen, methyl or ethyl, X represents nitrogen or C—$R^4$, wherein $R^4$ represents hydrogen, chlorine, fluorine or methoxy or together with $R^1$ can form a bridge of the structure —O—$CH_2$— or —S—$CH_2$—, Z represents radicals of the structures

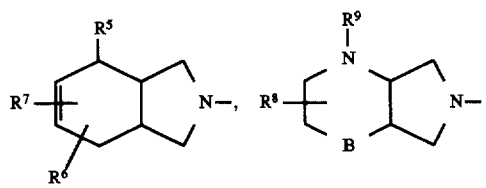

wherein $R^5$ represents hydrogen, hydroxyl, —$NR^{10}R^{11}$, hydroxymethyl, —$CH_2$—$NR^{10}R^{11}$, where $R^{10}$ represents hydrogen, methyl, alkoxycarbonyl having 1 to 4 C atoms in the alkoxy moiety or $C_1$–$C_3$-acyl, $R^{11}$ represents hydrogen or methyl, $R^6$ represents hydrogen, straight-chain or branched $C_1$–$C_3$-alkyl or cyclopropyl, $R^7$ represents hydrogen or methyl, $R^8$ represents hydrogen, $R^9$ represents hydrogen or methyl, B represents —$CH_2$—, O or a direct bond, and their pharmaceutically utilizable hydrates and acid addition salts and also the alkali metal, alkaline earth metal, silver and guanidinium salts of the carboxylic acids on which they are based.

If, for example, 7,8-difluoro-5-oxo-9,1-(epoxymethano)-5H-thiazolo[3,2-a]quinoline-4-carboxylic acid and 2,8-diazabicyclo-[4.3.0]-nonane are used for the preparation of compounds of the formula (I), the course of the reaction can be represented by the following equation:

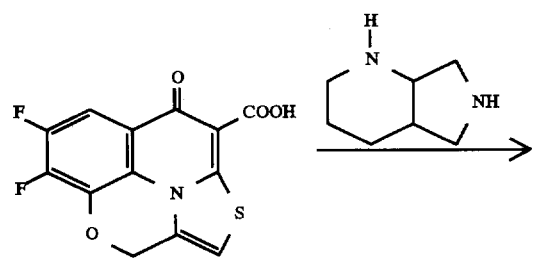

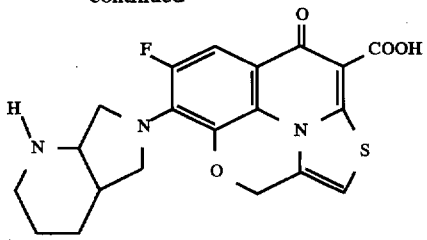

-continued

The compounds of the formula (II) used as starting compounds are known or can be prepared by known processes. They can optionally be employed as racemates, enantiomers or pure diastereomers.

Examples which may be mentioned are:

7,8-difluoro-5-oxo-5H-thiazolo[3,2a]quinoline-4-carboxylic acid,
7,8-difluoro-1-methyl-5-oxo-5H-thiazolo[3,2-a]quinoline-4-carboxylic acid,
7,8,9-trifluoro-1-methyl-5-oxo-5H-thiazolo[3,2-a]quinoline-4-carboxylic acid,
7,8-difluoro-5-oxo-9,1-(epoxymethano)-5H-thiazolo[3,2-a]quinoline-4-carboxylic acid,
7,8-difluoro-5-oxo-9,1-(epithiomethano)-5H-thiazolo[3,2-a]quinoline-4-carboxylic acid,
ethyl 7,8-difluoro-5-oxo-9,1-(epoxymethano)-5H-thiazolo[3,2-a]quinoline-4-carboxy-late,
ethyl 7,8-difluoro-5-oxo-9,1-(epithiomethano)-5H-thiazolo[3,2-a]quinoline-4-carboxy-late.

The amines of the formula (III) used as starting compounds are known. Chiral amines can be employed both as racemates and as enantiomerically pure or diastereomerically pure compounds.

Examples which may be mentioned are:

2,7-diazabicyclo[3.3.0]octane
2-methyl-2,7-diazabicyclo[3.3.0]octane
2,8-diazabicyclo[4.3.0]nonane
2-methyl-2,8-diazabicyclo[4.3.0]nonane
2-oxa-5,8-diazabicyclo[4.3.0]nonane
5-methyl-2-oxa-5,8-diazabicyclo[4.3.0]nonane.
2-amino-8-azabicyclo[4.3.0]non-3-ene
2-methylamino-8-azabicyclo[4.3.0]non-3-ene
4-methyl-2-methylamino-8-azabicyclo[4.3.0]non-3-ene
5-methyl-2-methylamino-8-azabicyclo[4.3.0]non-3-ene
2-dimethylamino-8-azabicyclo[4.3.0]non-3-ene
2-ethylamino-8-azabicyclo[4.3.0]non-3-ene
2-methylaminomethyl-8-azabicyclo[4.3.0]non-3-ene
2-hydroxy-8-azabicyclo[4.3.0]non-3-ene
5-isopropyl-2-methylamino-8-azabicyclo[4.3.0]non-3-ene
2-amino-5-isopropyl-8-azabicyclo[4.3.0]non-3-ene
2-amino-5-methyl-8-azabicyclo[4.3.0]non-3-ene
2-hydroxymethyl-8-azabicyclo[4.3.0]non-3-ene
2-amino-5-cyclopropyl-8-azabicyclo[4.3.0]non-3-ene The reaction of (II) with (III), in which the compounds (III) can also be employed in the form of their salts, such as e.g. the hydrochlorides, is preferably carried out in a diluent such as dimethyl sulphoxide, N,N-dimethylformamide, N-methylpyrrolidone, hexamethylphosphoramide, sulpholane, acetonitrile, water, an alcohol such as methanol, ethanol, n-propanol or isopropanol, glycol monomethyl ether or pyridine. Mixtures of these diluents can also be used.

Acid binders which can be used are all customary inorganic and organic acid binding agents. These preferably include the alkali metal hydroxides, alkali metal carbonates, organic amines and amidines. The following may be specifically mentioned as being particularly suitable: triethylamine, 1,4-diazabicyclo[2.2.2]octane (DABCO), 1,8-diazabicyclo[5.4.0]undec-7-ene (DBU) or excess amine (III).

The reaction temperatures can be varied within a relatively wide range. In general, the reaction is carried out at between about 20° and 200° C., preferably between 80° and 180° C.

The reaction can be carried out at normal pressure, but also at elevated pressure. In general, the reaction is carried out at pressures between 1 bar and 100 bar, preferably between 1 and 10 bar.

When carrying out the process according to the invention, 1 to 15 mol, preferably 1 to 6 mol, of the compound (III) are employed relative to 1 mol of the compound (II).

Free amino groups can be protected during reaction by a suitable amino protective group, for example by the tert.-butoxycarbonyl radical and liberated again after completion of the reaction by treatment with a suitable acid such as hydrochloric acid or trifluoroacetic acid (see Houben-Weyl, Methoden der Organischen Chemie, [Methods of Organic Chemistry], Volume E4, page 144 (1983); J. F. W. McOmie, Protective Groups in Organic Chemistry (1973), page 43).

The esters according to the invention are obtained by reaction of an alkali metal salt of the carboxylic acid on which they are based, which can optionally be protected on the N atom by protective groups such as the tert.-butoxycarbonyl radical, with suitable halogenoalkyl derivatives in a solvent such as dimethylformamide, dimethylacetamide, N-methylpyrrolidone, dimethyl sulphoxide or tetramethylurea at temperatures of about 0° to 100° C., preferably 0° to 50° C.

The acid addition salts of the compounds according to the invention are prepared in a customary manner, for example by dissolving the betaine in a sufficient amount of aqueous acid and precipitating the salt using a water-miscible organic solvent such as methanol, ethanol, acetone or acetonitrile. The equivalent amount of betaine and acid can also be heated in water or an alcohol such as glycol monoethyl ether, and the mixture can then be evaporated to dryness or the precipitated salts can be filtered off with suction. Pharmaceutically utilizable salts are understood as meaning, for example, the salts of hydrochloric acid, sulphuric acid, acetic acid, glycolic acid, lactic acid, succinic acid, citric acid, tartaric acid, methanesulphonic acid, 4-toluenesulphonic acid, galacturonic acid, gluconic acid, embonic acid, glutamic acid or aspartic acid. The compounds according to the invention can also be bound to acidic or basic ion exchangers.

The alkali metal or alkaline earth metal salts of the carboxylic acids according to the invention are obtained, for example, by dissolving the betaine in less than the stoichiometric amount of alkali metal or alkaline earth metal hydroxide solution, filtration of undissolved betaine and evaporation of the filtrate to dryness. Pharmaceutically suitable salts are those of sodium, potassium or calcium. The corresponding silver salts are obtained by reaction of an alkali metal or alkaline earth metal salt with a suitable silver salt, such as silver nitrate.

Combined with low toxicity, the compounds according to the invention have strong antibiotic activity and exhibit a broad antibacterial spectrum against gram-positive and gram-negative bacteria, in particular even against those which are resistant to various antibiotics, such as e.g. penicillins, cephalosporins, aminoglycosides, sulphonamides and tetracyclines.

These useful properties make possible their use as chemotherapeutic active compounds in medicine and veterinary medicine and also as substances for the preservation of inorganic or organic materials, in particular of organic materials of all types, e.g. polymers, lubricants, colourants, fibres, leather, paper and wood, of foodstuffs and of water.

The compounds according to the invention are active against a very wide spectrum of microorganisms. Using them gram-negative and gram-positive bacteria and bacteria-like microorganisms can be controlled, and the diseases caused by these pathogens can be prevented, ameliorated and/or cured.

The compounds according to the invention are distinguished by enhanced action on dormant and resistant bacteria. In the case of dormant bacteria, i.e. bacteria which show no detectable growth, the compounds act at concentrations below those of similar substances. This relates not only to the amount to be employed, but also to the rate of destruction. Such results were observed in the case of gram-positive and -negative bacteria, in particular in the case of Staphylococcus aureus, Micrococcus luteus and Enterococcus faecalis.

The compounds according to the invention exhibit surprising increases in action even against bacteria which are graded as less sensitive to comparable substances, in particular resistant Staphylococcus aureus and Enterococcus faecalis.

The compounds according to the invention are particularly active against bacteria and bacteria-like microorganisms. They are therefore particularly well suited for the prophylaxis and chemotherapy of local and systemic infections in human and veterinary medicine, which are caused by these pathogens.

The compounds are also suitable for the control of protozoonoses and helminthoses.

The compounds according to the invention can be administered in various pharmaceutical preparations. Preferred pharmaceutical preparations which may be mentioned are tablets, coated tablets, capsules, pills, granules, suppositories, injection and orally administrable solutions, suspensions and emulsions, and also pastes, ointments, gels, creams, lotions, powders and sprays.

Combined with favourable toxicity to warm-blooded animals, the active compounds are suitable preferably for the control of bacterial diseases which occur in animal keeping and animal breeding with productive, breeding, zoo, laboratory and experimental animals and pets. They are active here against all or individual stages of development and also against resistant and normally sensitive strains. As a result of the control of the bacterial diseases, illness, cases of death and yield decreases (e.g. in the production of meat, milk, wool, hides, eggs, honey, etc.) should be reduced such that more economical and simpler animal keeping is possible through the use of the active compounds.

The productive and breeding animals include mammals such as e.g. cattle, horses, sheep, pigs, goats, camels, water buffalo, donkeys, rabbits, fallow deer, reindeer, fur-bearing animals such as e.g. mink, chinchilla, racoons, birds such as e.g. hens, geese, turkeys, ducks, pigeons, species of bird for keeping at home and in zoos. They also include productive and ornamental fish.

The laboratory and experimental animals include mice, rats, guinea-pigs, golden hamsters, dogs and cats.

The pets include dogs and cats.

In general, it has proven advantageous to administer amounts from about 0.5 to about 50 mg, preferably 1 to 20 mg, of active compound per kg of body weight per day to achieve effective results.

The active compounds can also be administered together with the feed or drinking water of the animals.

Feedstuffs and foodstuffs contain 0.01 to 100 ppm, preferably 0.5 to 50 ppm, of the active compound in combination with a suitable edible material.

Such a feedstuff and foodstuff can be used both for healing purposes and also for prophylactic purposes.

Such a feedstuff or foodstuff is prepared by mixing a concentrate or a premix which contains 0.5 to 30%, preferably 1 to 20% by weight, of an active compound in a mixture with an edible organic or inorganic carrier with customary feedstuffs. Edible carriers are e.g. maize meal or maize and soya bean meal or mineral salts which preferably contain a small amount of an edible dust-prevention oil, e.g. maize oil or soya bean oil. The premix obtained here can then be added to the complete feedstuff before feeding it to the animals.

The minimum inhibitory concentrations (MIC) of the compounds according to the invention were determined by serial dilution methods on Iso-Sensitest Agar (Oxoid). For each test substance, a number of agar plates were prepared which, in each case at double the dilution, contained decreasing concentrations of the active compound. The agar plates were inoculated using a multipoint inoculator (Denley). For inoculation, overnight cultures of the pathogens were used which had previously been diluted such that each inoculation point contained about $10^4$ colony-forming particles. The inoculated agar plates were incubated at 37° C., and the bacterial growth was read off after about 20 hours.

The MIC value (μg/ml) indicates the lowest active compound concentration at which no growth was to be observed using the naked eye.

In the table below, the MIC values of some of the compounds according to the invention are shown.

TABLE

MIC values

| Species | Strain | Example No. 2 | 3 | 4 | 5 |
|---|---|---|---|---|---|
| E. coli | Neumann | ≦0.015 | ≦0.015 | ≦0.015 | ≦0.015 |
|  | ATCC 25922 | ≦0.015 | ≦0.015 | ≦0.015 | ≦0.015 |
| Klebsiella pneumonia | 8085 | ≦0.015 | ≦0.015 | ≦0.015 | ≦0.015 |
|  | 63 | ≦0.015 | ≦0.015 | ≦0.015 | ≦0.015 |
| Providencia sp. | 12012 | ≦0.015 | ≦0.015 | ≦0.015 | ≦0.015 |
| Micrococcus luteus | 9341 | 0.125 | ≦0.015 | ≦0.015 | ≦0.015 |
| Staphylococcus aureus | ICB 25701 | 0.5 | 0.06 | 0.06 | 0.06 |
|  | ATCC29213 | ≦0.015 | ≦0.015 | ≦0.015 | ≦0.015 |
|  | 133 | ≦0.015 | ≦0.015 | ≦0.015 | ≦0.015 |
|  | ICB 25768 | 32 | 0.5 | 0.25 | 0.5 |
| Enterococcus faecalis | 27101 | 0.03 | ≦0.015 | ≦0.015 | ≦0.015 |
|  | 9790 | 0.03 | ≦0.015 | ≦0.015 | ≦0.015 |

Preparation of the active compounds

EXAMPLE 1

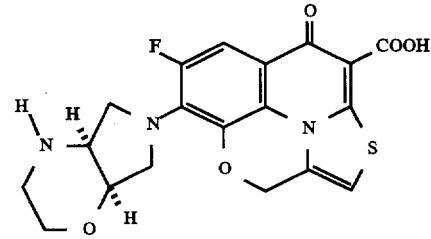

7-Fluoro-8-[1R,6S)-2-oxa-5,8-diazabicyclo[4.3.0] nonan-8-yl]-5-oxo-9,1-(epoxymethano)-5H-thiazolo [3,2-a]quinoline-4-carboxylic acid 100 mg (0.323 mmol) of 7,8-difluoro-5-oxo-9,1-(epoxymethano)-5H-thiazolo[3,2-a]-quinoline-4-carboxylic acid are heated at 100° C. under argon for 2 hours with 62 mg (0.48 mmol) of (1R,6S)-2-oxa-5,8-diazabicyclo-[4.30] nonane in 3 ml of dimethyl sulphoxide. The mixture is concentrated in a high vacuum, the residue is recrystallized from ethanol and the product is dried.

Yield: 113 mg (84% of theory)

Melting point: >300° C.

EXAMPLE 2

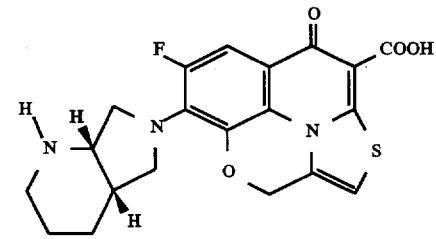

8-[1S,6S)-2,8-Diazabicyclo[4.3.0]nonan-8-yl]-7-fluoro-5-oxo-9,1-(epoxymethano)-5H-thiazolo[3.2-a]quinoline-4-carboxylic acid Analogously to Example 1, the title compound is obtained in the reaction with (1S,6S)-2,8-diazabicyclo-[4.3.0]nonane.

Melting point: 270°–278° C. (with decomposition)

EXAMPLE 3

7-Fluoro-8-(2-methylamino-8-azabicyclo[4.3.0]non-3-en-8-yl)-5-oxo-9,1-(epoxymethano)-5H-thiazolo [3,2-a]quinoline-4-carboxylic acid Analogously to Example 1, the title compound is obtained in the reaction with 2-methylamino-8-azabicyclo-[4.3.0] non-3-ene.

9

Melting point: 260°–273° C.

EXAMPLE 4

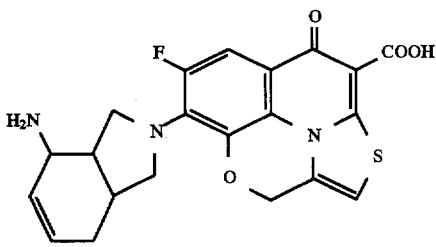

8-(2-Amino-8-azabicyclo[4.3.0]non-3-en-8-yl)-7-fluoro-5-oxo-9,1-(epoxymethano)-5H-thiazolo[3,2-a]quinoline-4-carboxylic acid 100 mg (0.323 mmol) of 7,8-difluoro-5-oxo-9,1-(epoxymethano)-5H-thiazolo[3,2-a]-quinoline-4-carboxylic acid are heated at 80° C. under argon for 4 hours with 67 mg (0.48 mmol) of 2-amino-8-azabicyclo[4.3.0]non-3-ene in 3 ml of DMSO. The mixture is concentrated in a high vacuum, the residue is recrystallized from ethanol and the product is dried.

Yield: 127 mg (92% of theory)

Melting point: 280° C. (with decomposition).

EXAMPLE 5

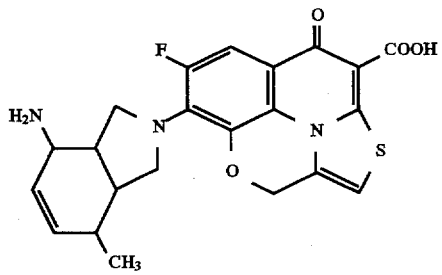

8-(2-Amino-5-methyl-8-azabicyclo[4.3.0]non-3-en-8-yl)-7-fluoro-5-oxo-9,1-(epoxymethano)-5H-thiazolo[3,2-a]quinoline-4-carboxylic acid Analogously to Example 4, the title compound is obtained in the reaction with 2-amino-5-methyl-8-azabicyclo[4.3.0]non-3-ene.

Melting point: 240°–250° C.

EXAMPLE 6

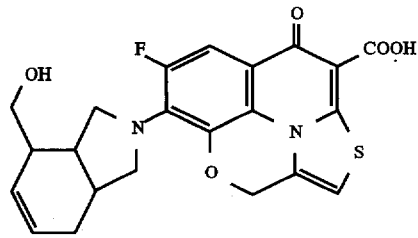

7-Fluoro-8-(2-hydroxymethyl-8-azabicyclo[4.3.0]non-3-en-8-yl)-5-oxo-9,1-(epoxymethano)-5H-thiazolo[3,2-a]quinoline-4-carboxylic acid Analogously to Example 1, the title compound is obtained in the reaction with 2-hydroxymethyl-8-azabicyclo[4.3.0]non-3-ene.

10

Melting point: 290°–293° C.

EXAMPLE 7

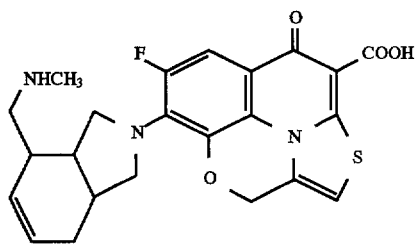

7-Fluoro-8-(2-methylaminomethyl-8-azabicyclo[4.3.0]non-3-en-8-yl)-5-oxo-9,1-(epoxymethano)-5H-thiazolo[3,2-a]quinoline-4-carboxylic acid Analogously to Example 1, the title compound is obtained in the reaction with 2-methylaminomethyl-8-azabicyclo[4.3.0]non-3-ene.

Melting point: 215°–218° C.

EXAMPLE 8

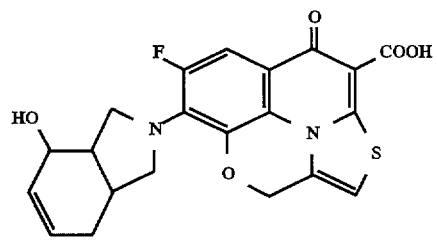

7-Fluoro-8-(2-hydroxy-8-azabicyclo[4.3.0]non-3-en-8-yl)-5-oxo-9,1-(epoxymethano)-5H-thiazolo[3,2-a]quinoline-4-carboxylic acid 100 mg (0.323 mmol) of 7,8-difluoro-5-oxo-9,1-(epoxymethano)-5H-thiazolo[3,2-a]-quinoline-4-carboxylic acid are heated at 120° C. under argon for 6 hours with 90 mg (0.65 mmol) of 2-hydroxy-8-azabicyclo[4.3.0]non-3-ene in 3 ml of DMSO. The mixture is concentrated in a high vacuum, the residue is recrystallized from ethanol and the product is dried.

Yield: 23 mg (17% of theory)

Melting point: >300° C.

EXAMPLE 9

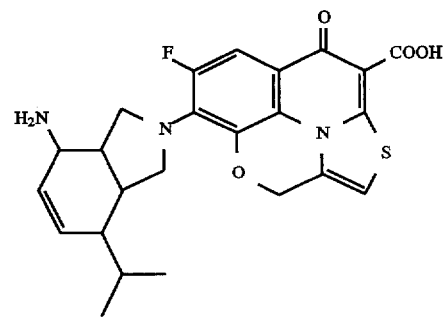

8-(2-Amino-5-isopropyl-8-azabicyclo[4.3.0]non-4-en-8-yl)-7-fluoro-5-oxo-9,1-(epoxymethano)-5H-thiazolo[3,2-a]quinoline-4-carboxylic acid Analogously to Example 4, the title compound is obtained in the reaction with 2-amino-5-isopropyl-8-azabicyclo[4.3.0]non-4-ene.

Melting point: 265° C. (with decomposition)

EXAMPLE 10

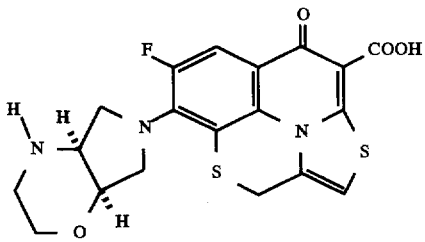

7-Fluoro-8-((1R,6S)-2-oxa-5,8-diazabicyclo[4.3.0]nonan-8-yl)-5-oxo-9,1-(epithiomethano)-5H-thiazolo[3,2-a]quinoline-4-carboxylic acid 100 mg (0.307 mmol) of 7,8-difluoro-5-oxo-9,1-(epithiomethano)-5H-thiazolo[3,2-a]-quinoline-4-carboxylic acid are heated at 120° C. under argon for 3 hours with 59 mg (0.46 mmol) of (1R,6S)-2-oxa-5,8-diazabicyclo[4.3.0]nonane in 3 ml of dimethyl sulphoxide. The mixture is concentrated in a high vacuum, the residue is recrystallized from ethanol and the product is dried.

Yield: 98 mg (74% of theory)

Melting point: 235°–238° C. (with decomposition)

EXAMPLE 11

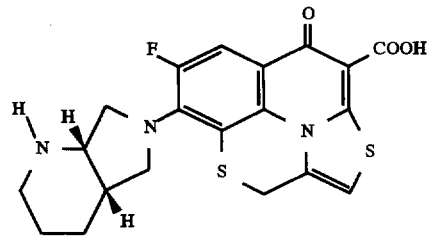

8-((1S,6S)-2,8-Diazabicyclo[4.3.0]nonan-8-yl)-7-fluoro-5-oxo-9,1-(epithiomethano)-5H-thiazolo[3,2-a]quinoline-4-carboxylic acid Analogously to Example 10, the title compound is obtained in the reaction with (1S,6S)-2,8-diazabicyclo[4.3.0]nonane.

Melting point: 242°–244° C. (with decomposition)

EXAMPLE 12

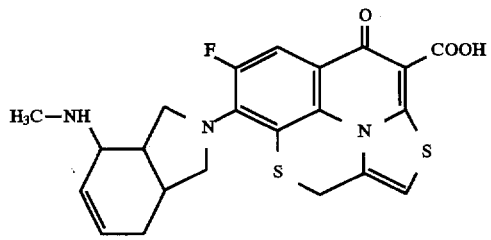

7-Fluoro-8-(2-methylamino-8-azabicyclo[4.3.0]non-3-en-8-yl)-5-oxo-9,1-(epithiomethano)-5H-thiazolo[3,2-a]quinoline-4-carboxylic acid Analogously to Example 10, the title compound is obtained in the reaction with 2-methylamino-8-azabicyclo[4.3.0]non-3-ene.

Melting point: >300° C.

EXAMPLE 13

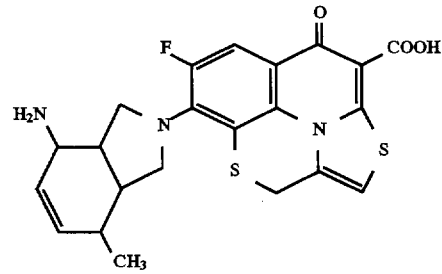

8-(2-Amino-5-methyl-8-azabicyclo[4.3.0]non-3-en-8-yl)-7-fluoro-5-oxo-9,1-(epithiomethano)-5H-thiazolo[3,2-a]quinoline-4-carboxylic acid Analogously to Example 10, the title compound is obtained in the reaction with 2-amino-5-methyl-8-azabicyclo[4.3.0]non-3-ene.

Melting point: 148°–152° C. (with decomposition)

EXAMPLE 14

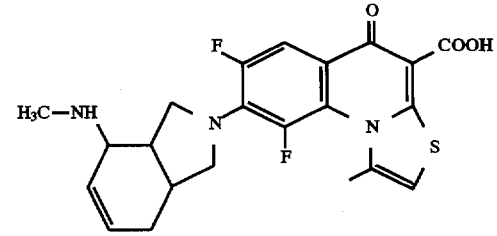

7,9-Difluoro-1-methyl-8-(2-methylamino-8-azabicyclo[4.3.0]non-3-en-8-yl)-5-oxo-5H-thiazolo[3.2-a]quinoline-4-carboxylic acid 100 mg (0.318 mmol) of 7,8,9-trifluoro-1-methyl-5-oxo-5H-thiazolo[3,2-a]quinoline-4-carboxylic acid are heated at 80° C. under argon for 2 hours with 97 mg (0.64 mmol) of 2-methylamino-8-azabicyclo[4.3.0]-non-3-ene in 3 ml of DMSO. The mixture is concentrated in a high vacuum, the residue is recrystallized from ethanol and the product is dried.

Yield: 107 mg (76% of theory)
Melting point: >300° C.

EXAMPLE 15

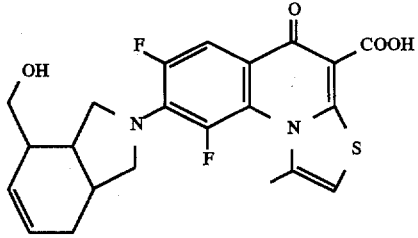

7,9-Difluoro-8-(2-hydroxymethyl-8-azabicyclo[4.3.0]non-3-en-8-yl)-1-methyl-5-oxo-5H-thiazolo[3,2-a]quinoline-4-carboxylic acid Analogously to Example 14, the title compound is obtained in the reaction with 2-hydroxymethyl-8-azabicyclo[4.3.0]non-3-ene.

Melting point: 220°–221° C.

EXAMPLE 16

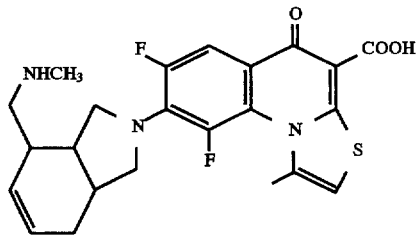

7,9-Difluoro-1-methyl-8-(2-methylaminomethyl-8-azabicyclo[4.3.0]non-3-en-8-yl)-5-oxo-5H-thiazolo[3,2-a]quinoline-4-carboxylic acid Analogously to Example 14, the title compound is obtained in the reaction with 2-methylaminomethyl-8-azabicyclo[4.3.0]non-3-ene.

Melting point: 270°–273° C. (with decomposition)

EXAMPLE 17

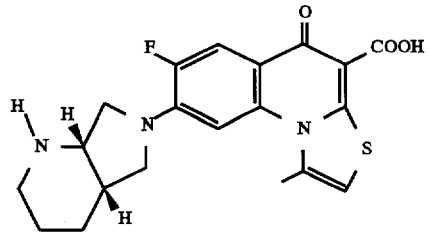

8-((1S,6S)-2,8-Diazabicyclo[4.3.0]nonan-8-yl)7-fluoro-1-methyl-5-oxo-5H-thiazolo[3,2-a]quinoline-4-carboxylic acid Analogously to Example 14, the title compound is obtained in the reaction with 7,8-difluoro-1-methyl-5-oxo-5H-thiazolo[3,2-a]quinoline-4-carboxylic acid with (1S,6S)-2,8-diazabicyclo[4.3.0]nonane.

Melting point: 288°–290° C. (with decomposition)

EXAMPLE 18

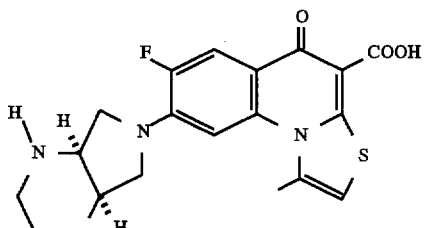

7-Fluoro-1-methyl-8-((1R,6S)-2-oxa-5,8-diazabicyclo[4.3.0]nonan-8-yl)-5-oxo-5H-thiazolo[3,2-a]quinoline-4-carboxylic acid Analogously to Example 14, the title compound is obtained in the reaction with 7,8-difluoro-1-methyl-5-oxo5H-thiazolo[3,2-a]quinoline-4-carboxylic acid with (1R,6S)-2-oxa-5,8-diazabicyclo[4.3.0]nonane.

Melting point: >300° C.

EXAMPLE 19

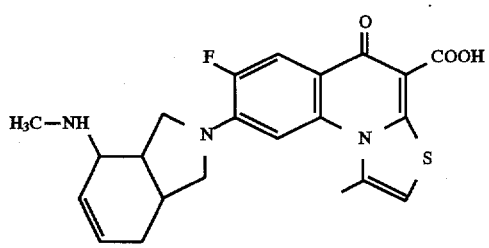

7-Fluoro-1-methyl-8-(2-methylamino-8-azabicyclo[4.3.0]non-3-en-8-yl)-5-oxo-5H-thiazolo[3,2-a]quinoline-4-carboxylic acid Analogously to Example 14, the title compound is obtained in the reaction with 7,8-difluoro-1-methyl-5-oxo-5H-thiazolo[3,2-a]quinoline-4-carboxylic acid with 2-methylamino-8-azabicyclo[4.3.0]non-3-ene.

Melting point: 270°–272° C. (with decomposition)

EXAMPLE 20

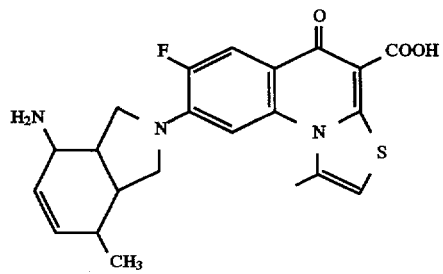

8-(2-Amino-5-methyl-8-azabicyclo[4.3.0]non-3-en-8-yl)-7-fluoro-1-methyl-5-oxo-5H-thiazolo[3,2-a]quinoline-4-carboxylic acid Analogously to Example 14, the title compound is obtained in the reaction with 7,8-difluoro-1-methyl-5-oxo- 5H-thiazolo[3,2-a]quinoline-4-carboxylic acid with 2-amino-5-methyl-8-azabicyclo[4.3.0]non-3-ene.

Melting point: 263°–268° C. (with decomposition).

We claim:

1. The compounds of the formula (I)

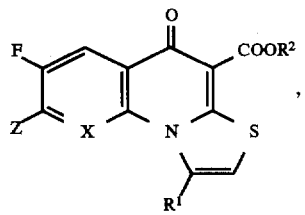

in which

R¹ represents hydrogen or methyl which is optionally substituted by halogen or methoxy, R² represents hydrogen, alkyl having 1 to 4 carbon atoms which is optionally substituted by hydroxyl, methoxy, amino, methylamino or dimethylamino, or (5-methyl-2-oxo-1,3-dioxol-4-yl)methyl, X represents nitrogen or C—R⁴, wherein
    R⁴ represents hydrogen, halogen or methoxy or together with R¹ can form a bridge of the structure —O—CH₂— or —S—CH₂—, Z represents the radicals of the structures

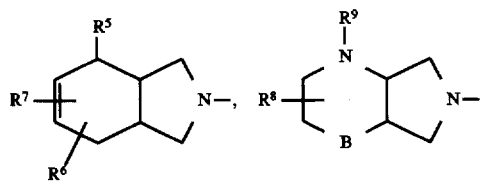

wherein

R⁵ is represents hydrogen, hydroxyl, —NR¹⁰R¹¹, hydroxymethyl, —CH₂—NR¹⁰R¹¹, carboxyl, methoxycarbonyl or ethoxycarbonyl, where
    R¹⁰ represents hydrogen, C₁–C₃-alkyl, which is optionally substituted by hydroxyl, alkoxycarbonyl having 1 to 4 C atoms in the alkoxy moiety or C₁–C₃-acyl,
    R¹¹ represents hydrogen or methyl, R⁶ represents hydrogen, straight-chain or branched C₁–C₃-alkyl or cyclopropyl, R⁷ represents hydrogen or methyl, R⁸ represents hydrogen or methyl, R⁹ represents hydrogen, methyl or radicals of the structures —CH=CH—COOR⁹', —CH₂—CH₂—COOR⁹', —CH₂—CO—CH₃, —CH₂—CH₂—CN,
    R⁹' represents methyl or ethyl, B represents —CH₂—, O or a direct bond, or a pharmaceutically utilizable hydrate or acid addition salt thereof, or an alkali metal, alkaline earth metal, silver or guanidinium salt of the carboxylic acid on which it is based.

2. The process for the preparation of the compounds of the formula (I) according to claim 1

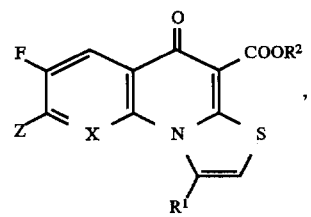

in which

R¹ represents hydrogen or methyl which is optionally substituted by halogen or methoxy, R² represents hydrogen, alkyl having 1 to 4 carbon atoms which is optionally substituted by hydroxyl, methoxy, amino, methylamino or dimethylamino, or (5-methyl-2-oxo-1,3-dioxol-4-yl)-methyl, X represents nitrogen or C—R⁴, wherein
    R⁴ represents hydrogen, halogen or methoxy or together with R¹ can form a bridge of the structure —O—CH₂— or —S—CH₂—, Z represents the radicals of the structures

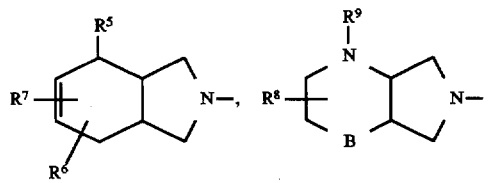

wherein

R⁵ represents hydrogen, hydroxyl, —NR¹⁰R¹¹, hydroxymethyl, —CH₂—NR¹⁰R¹¹, carboxyl, methoxycarbonyl or ethoxycarbonyl, where
    R¹⁰ represents hydrogen, C₁–C₃-alkyl, which is optionally substituted by hydroxyl, alkoxycarbonyl having 1 to 4 C atoms in the alkoxy moiety or C₁–C₃-acyl,
    R¹¹ represents hydrogen or methyl, R⁶ represents hydrogen, straight-chain or branched C₁–C₃-alkyl or cyclopropyl, R⁷ represents hydrogen or methyl, R⁸ represents hydrogen or methyl, R⁹ represents hydrogen, methyl or radicals of the structures —CH=CH—COOR⁹', —CH₂—CH₂—COOR⁹', —CH₂—CO—CH₃, —CH₂—CH₂—CN,
    R⁹' represents methyl or ethyl, B represents —CH₂—, O or a direct bond, wherein compounds of the formula (II)

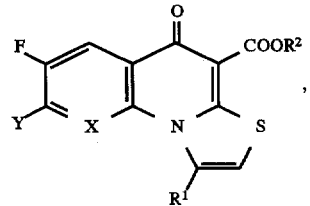

in which

R¹, R² and X have the meaning indicated above and

Y represents fluorine or chlorine, are reacted with compounds of the formula (III)

Z-H          (III), in which

Z has the meaning indicated above, if appropriate in the presence of acid scavengers.

3. Compounds of the formula (I) according to claim 1, in which $R^1$ represents hydrogen or methyl, $R^2$ represents hydrogen, alkyl having 1 to 4 carbon atoms, which is optionally substituted by hydroxyl, methoxy, amino, methylamino or dimethylamino, or (5-methyl-2-oxo-1,3-dioxol-4-yl)-methyl, X represents nitrogen or C—$R^4$, wherein
 $R^4$ represents hydrogen, halogen or methoxy or together with $R^1$ can form a bridge of the structure —O—$CH_2$— or —S—$CH_2$—, Z represents radicals of the structures

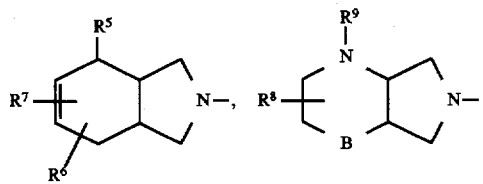

wherein $R^5$ represents hydrogen, hydroxyl, —$NR^{10}R^{11}$, hydroxymethyl, —$CH_2$—$NR^{10}R^{11}$, where
 $R^{10}$ represents hydrogen, $C_1$-$C_2$-alkyl which is optionally substituted by hydroxyl, alkoxycarbonyl having 1 to 4 C atoms in the alkoxy moiety or $C_1$-$C_3$-acyl,
 $R^{11}$ represents hydrogen or methyl, $R^6$ represents hydrogen, straight-chain or branched $C_1$-$C_3$-alkyl or cyclopropyl, $R^7$ represents hydrogen or methyl, $R^8$ represents hydrogen, $R^9$ represents hydrogen or methyl, B represents —$CH_2$—, O or a direct bond, or a pharmaceutically utilizable hydrate or acid addition salt thereof, or an alkali metal, alkaline earth metal, silver or guanidinium salt of the carboxylic acid on which it is based.

4. Compounds of the formula (I) according to claim 1, in which $R^1$ represents methyl, $R^2$ represents hydrogen, methyl or ethyl, X represents nitrogen or C—$R^4$, wherein
 $R^4$ represents hydrogen, chlorine, fluorine or methoxy or together with $R^1$ can form a bridge of the structure —O—$CH_2$— or —S—$CH_2$—, Z represents radicals of the structures

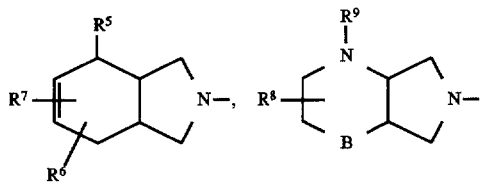

wherein $R^5$ represents hydrogen, hydroxyl, —$NR^{10}R^{11}$, hydroxymethyl, —$CH_2$—$NR^{10}R^{11}$, where
 $R^{10}$ represents hydrogen, methyl, alkoxycarbonyl having 1 to 4 C atoms in the alkoxy moiety or $C_1$-$C_3$-acyl,
 $R^{11}$ represents hydrogen or methyl, $R^6$ represents hydrogen, straight-chain or branched $C_1$-$C_3$-alkyl or cyclopropyl, $R^7$ represents hydrogen or methyl, $R^8$ represents hydrogen, $R^9$ represents hydrogen or methyl, B represents —$CH_2$—, O or a direct bond, or a pharmaceutically utilizable hydrate or acid addition salt thereof, or an alkali metal, alkaline earth metal, silver or guanidinium salt of the carboxylic acid on which it is based.

5. An antibacterial composition comprising an antibacterial effective amount of a compound of the formula (I) according to claim 1 in combination with a pharmaceutically acceptable carrier or exipient.

6. The process for producing an antibacterial formulation comprising combining the compounds of the formula (I) according to claim 1 with a pharmaceutically acceptable carrier or exipient.

7. A method for combating a bacterial infection in a host comprising administering to said host an effective amount therefor of a compound of the formula (I) according to claim 1.

* * * * *